United States Patent
Bui et al.

(10) Patent No.: US 8,741,276 B2
(45) Date of Patent: *Jun. 3, 2014

(54) COMFORTABLE, LONG WEARING COLORED COSMETIC COMPOSITIONS

(75) Inventors: Hy Si Bui, Piscataway, NJ (US); Susan Halpern, Paramus, NJ (US); Mohamed Kanji, Edison, NJ (US)

(73) Assignee: L'Oréal (FR)

( * ) Notice: Subject to any disclaimer, the term of this patent is extended or adjusted under 35 U.S.C. 154(b) by 498 days.

This patent is subject to a terminal disclaimer.

(21) Appl. No.: 12/131,250

(22) Filed: Jun. 2, 2008

(65) Prior Publication Data

US 2008/0305067 A1 Dec. 11, 2008

Related U.S. Application Data

(60) Provisional application No. 60/942,359, filed on Jun. 6, 2007.

(51) Int. Cl.
*A61K 8/81* (2006.01)
*A61K 8/891* (2006.01)
*A61Q 1/02* (2006.01)
*A61Q 1/06* (2006.01)

(52) U.S. Cl.
CPC ............. *A61K 8/8117* (2013.01); *A61K 8/891* (2013.01); *A61Q 1/02* (2013.01); *A61Q 1/06* (2013.01)
USPC ............. 424/78.02; 424/78.03; 424/78.37; 424/70.121

(58) Field of Classification Search
None
See application file for complete search history.

(56) References Cited

U.S. PATENT DOCUMENTS

| | | | |
|---|---|---|---|
| 5,492,945 A | 2/1996 | Morita et al. | |
| 5,538,793 A | 7/1996 | Inokuchi et al. | |
| 5,756,568 A | 5/1998 | Morita et al. | |
| 5,945,471 A | 8/1999 | Morita et al. | |
| 6,280,748 B1 | 8/2001 | Morita et al. | |
| 6,376,078 B1 | 4/2002 | Inokuchi | |
| 6,517,818 B1* | 2/2003 | Golz-Berner et al. | 424/64 |
| 2004/0156806 A1 | 8/2004 | Patil et al. | |
| 2004/0180011 A1 | 9/2004 | Schlosser | |
| 2005/0180931 A1 | 8/2005 | Oguchi et al. | |
| 2005/0220728 A1 | 10/2005 | Kanji et al. | |
| 2006/0013839 A1* | 1/2006 | Yu | 424/401 |
| 2006/0110347 A1 | 5/2006 | Lu et al. | |
| 2006/0292096 A1* | 12/2006 | Yu | 424/64 |
| 2007/0093619 A1 | 4/2007 | Bui et al. | |
| 2007/0142521 A1 | 6/2007 | Brahms et al. | |
| 2007/0149703 A1* | 6/2007 | Caprasse et al. | 524/588 |
| 2008/0305061 A1 | 12/2008 | Bui et al. | |
| 2008/0305062 A1 | 12/2008 | Bui et al. | |
| 2008/0305064 A1 | 12/2008 | Bui et al. | |

FOREIGN PATENT DOCUMENTS

WO 2005/090444 9/2005
WO 2005/100444 10/2005

OTHER PUBLICATIONS

Dow Corning, "DC670" (http://www.dowcorning.com/applications/search/default.aspx?R=2222EN), accessed Aug. 10, 2011.*
"Dow Corning 670 Fluid", Ref. No. 27-1158-01 (2004).*
International Cosmetic Ingredient Dictionary and Handbook, 9th edition, 2002 pp. 2903-2906, published by The Cosmetic, Toiletry, and Fragrance Association, 1101 17th Street, NW, Suite 300, Washington, DC 20036.
Factsheet—Dow Corning 670 Fluid—Intellectual Property Statement—Apr. 14, 2005.
Virginie Caprasse, Isabelle Van Reeth, Dow Corning S.A., Research Disclosure, A new silicone resin for personal care applications, Research Disclosure Database No. 486008, Published in Oct. 2004 (Electronic publication date: Sep. 10, 2004), Research Disclosure Journal, Kenneth Mason Publications Ltd., The Book Barn, Westbourne, Hants. PO10 8RS UK.
Kirk-Othmer, Encyclopedia of Chemical Technology, vol. 22, pp. 333-432, 3rd edition, 1979, A Wiley-Interscience publication, John Wiley and Sons.

* cited by examiner

*Primary Examiner* — Daniel Sullivan
*Assistant Examiner* — Barbara Frazier
(74) *Attorney, Agent, or Firm* — Lerner, David, Littenberg, Krumholz & Mentlik, LLP

(57) ABSTRACT

The present invention is directed to a composition containing: (a) at least one tackifier component having a glass transition temperature ($T_g$) of greater than about 20° C.; (b) at least one film former chosen from a propylphenylsilsesquioxane resin having a molecular weight of from about 2,000 to about 30,000 and comprising at least about 70 mole % propyl siloxy units and at most about 30 mole % phenyl siloxy units, and a propylsilsesquioxane wax substituted with alkyl units having at least 30 carbons; (c) a liquid fatty phase comprising at least one volatile hydrocarbon compound; (d) at least one colorant; (e) optionally, water; and (f) optionally, at least one emulsifier. Also disclosed is a method of making up keratinous substrates involving applying the above composition onto the keratinous substrates.

20 Claims, No Drawings

COMFORTABLE, LONG WEARING COLORED COSMETIC COMPOSITIONS

This application is based on and claims the benefit of U.S. Provisional Application Ser. No. 60/942,359, entitled COMFORTABLE, LONG WEARING COLORED COSMETIC COMPOSITIONS, filed Jun. 6, 2007, the entire disclosure of which is incorporated by reference herein.

BACKGROUND OF THE INVENTION

The present invention is directed to a colored cosmetic composition used to make up a user's keratinous substrate. Colored cosmetic compositions typically contain film forming resins which enable the cosmetic product to adhere to, and remain on, the keratinous substrate to which it is applied. The ability of a cosmetic product to remain on keratinous substrates is commonly referred to by the terms "transfer resistance" and "long wearing".

The problem with conventional film forming resins, however, is that they are uncomfortable to wear and have a tendency to be brittle and to flake off. In an effort to overcome these drawbacks, a plasticizer is employed in order to impart flexibility to the resin. Unfortunately, the use of a plasticizer has a negative impact on the transfer resistance of the colored cosmetic product, i.e., the product comes off the keratinous substrate when in contact with another surface.

Thus, it is an object of the present invention to provide a method and composition for making up keratinous substrates in a manner which delivers a combination of long wear, transfer resistance and comfort with little, if any, tackiness.

BRIEF SUMMARY OF THE INVENTION

A first aspect of the present invention is directed to a composition for making up keratinous substrates containing: (a) at least one tackifier component having a glass transition temperature ($T_g$) of greater than about 20° C.; (b) at least one film former chosen from a propylphenylsilsesquioxane resin having a molecular weight of from about 2,000 to about 30,000, and comprising at least about 70 mole % propyl siloxy units and at most about 30 mole % phenyl siloxy units, based on the total mole % siloxy units of the resin, and a propylsilsesquioxane wax substituted with alkyl units having at least 30 carbons; (c) a liquid fatty phase comprising at least one volatile hydrocarbon compound; (d) at least one colorant; (e) optionally, water; and (f) optionally, at least one emulsifier.

A second aspect of the present invention is directed to a method of making up keratinous substrates comprising applying onto the substrates the above-disclosed cosmetic composition.

It has been surprisingly discovered that the use of the above-disclosed colored cosmetic composition delivers a combination of long wear, transfer resistance and comfort.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Transfer resistance" as used herein refers to the quality exhibited by compositions that are not readily removed by contact with another material, such as, for example, a drinking glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred from a wearer to any other substrate, such as transfer from the neck of an individual to a collar after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. Further, the amount transferred may be compared with that transferred by other compositions, such as commercially available compositions. In a preferred embodiment of the present invention, little or no composition is transferred to the substrate.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Tackiness", as used herein, refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Keratinous substrates", as used herein, include but are not limited to, skin, hair and nails.

The phrase "liquid fatty phase" is understood to mean a fatty phase, which is liquid at room temperature (25° C.) and atmospheric pressure (760 mmHg), and which comprises one or more fatty substances that are liquid at room temperature, also known as oils, which are compatible with one another.

Tackifier

The compositions of the present invention comprise at least one tackifier component. In general, tackifiers can be divided into four different families in terms of their chemistry: hydrocarbon resins, terpenes, amorphous (i.e. non-crystalline) rosins, rosin esters and their derivatives, and pure monomer resins.

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar. (Non-polar meaning that the tackifier is substantially free of monomers having polar groups. Preferably, the polar groups are not present, however, if they are present, they are preferably present in an amount of up to about 5% by weight, preferably up to about 2% by weight, and more preferably up to about 0.5% by weight.)

In some embodiments, the tackifier may have a softening point (Ring and Ball, as measured by ASTM E-28) of 80° C. to 150° C., preferably 100° C. to 130° C. In other embodiments the tackifier may be liquid and have an R and B softening point of between about −70° C. and 70° C.

In some embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all of which are commercially available from Eastman Chemical under the trade name Regalite®. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may be employed without departing from the spirit of the invention.

A particularly preferred tackifier for use in the present invention is a hydrogenated hydrocarbon resin such, for example, a hydrogenated styrene/methyl styrene/indene copolymer, commercially available from Eastman under the tradename Regalite® R1100.

The tackifier is present in the composition of the invention in an amount ranging from greater than about 0% to about 70% by weight; greater than about 0% to about 60% by weight; greater than about 0% to about 50% by weight; greater than about 0% to about 40%; greater than about 0% to about 30% by weight; greater than about 0% to about 20% by weight; greater than 0 to about 10% by weight, all weights based on the weight of the composition as a whole.

Film Former

Propylphenylsilsesquioxane Resin

Silsesquioxane resins are a specific form of silicone resins. Silicone resins are crosslinked organopolysiloxanes which are solid at room temperature and generally soluble in organic solvents. When they are soluble in volatile solvents, silicone resins are capable of forming a film once the solvent has evaporated. Furthermore, if the solvent dissolving the silicone resin is absorbed on the substrate onto which it is applied, the silicone resin which remains on the substrate may also form a film.

The compositions of the present invention comprise propylphenylsilsesquioxane resins, which have been disclosed in patent publications WO2005/090444, published on Sep. 29, 2005; US20040180011, published on Sep. 16, 2004; and US20040156806, published on Aug. 12, 2004, the entire contents of each of which are hereby incorporated by reference.

The propylphenylsilsesquioxane resin comprises propyl siloxy units $(C_3H_7SiO_{3/2})$ and phenyl siloxy units $(C_6H_5SiO_{3/2})$. The propylphenylsilsesquioxane resin contain at least about 70 mole % of propyl siloxy units, based on the total mole % siloxy units of the resin, and at most about 30 mole % of phenyl siloxy units, based on the total mole % siloxy units of the resin.

The propylphenylsilsesquioxane resin will have a weight average molecular weight of from about 2,000 to about 30,000, such as from about 3,000 to about 20,000.

The propylphenylsilsesquioxane resins preferably soften in the range of from about 30° C. to about 100° C., such as from about 30° C. to about 80° C., and such as from about 40° C. to about 70° C., as determined by DIN 53180 "Softening Point of Resins".

The mole % of propyl siloxy units to phenyl siloxy units can be adjusted depending on an intended application. As such, it is possible to have propylphenylsilsesquioxane resins having a mole % propyl siloxy units:phenyl siloxy units ranging from about 70:30 to about 100:0, such as 70:30; 80:20; 90:10; and 100:0; and subranges therebetween. When the mole % of the propyl siloxy units is about 100 mole %, the propylphenylsilsesquioxane resin is referred to as a propylsilsesquioxane resin.

A suitable example of propylsilsesquioxane resin for use in cosmetic composition of the present invention includes, but is not limited to, a propylsilsesquioxane resin commercially available from Dow-Corning under the tradename DC 670 Fluid.

Propylsilsesquioxane Wax Substituted with Alkyl Units Having at Least 30 Carbons The compositions of the present invention comprise propylsilsesquioxane waxes which have been disclosed in patent publication WO2005/100444, published on Oct. 27, 2005, the entire contents of which is hereby incorporated by reference.

It should be noted, however, that not all propylsilsesquioxane waxes yield stable colored cosmetic emulsion products. More particularly, it has been found that only those propylsilsesquioxane waxes substituted with alkyl units having at least 30 carbons are stable.

The propylsilsesquioxane wax comprises at least 40 mole of siloxy units having the formula $(R_2R'SiO_{1/2})_x(C_3H_7SiO_{3/2})_y$, where x and y have a value of 0.05 to 0.95, R is an alkyl group having from 1 to 8 carbon atoms, R' is a monovalent hydrocarbon having 30 to 40 carbon atoms and greater. As used herein, x and y represent the mole fraction of $(R_2R'SiO_{1/2})$ and $(C_3H_7SiO_{3/2})$ siloxy units relative to each other present in the propylsilsesquioxane wax. Thus, the mole fraction of ($R_2R'SiO_{1/2}$) and ($C_3H_7SiO_{3/2}$) siloxy units each can independently vary from 0.05 to 0.95. Preferably R is a methyl, and R' is an alkyl having at least 30 carbons, available from Dow Corning.

Typically, the value of x is 0.05 to 0.95, or alternatively, 0.2 to 0.8, the value of y is 0.05 to 0.95, alternatively 0.2 to 0.8. However, the combination of ($R_2R'SiO_{1/2}$) and ($C_3H_7SiO_{3/2}$) siloxy units present must total at least 40 mole %, alternatively 60 mole %, or alternatively 90 mole % of all siloxy units present in the propylsilsesquioxane wax.

The number average molecular weight of the propylsilsesquioxane wax substituted with alkyl units having at least 30 carbons typically ranges from about 750 to about 10,000, such as from about 1,000 to about 5,000.

In some embodiments, the amounts and/or ratios of the tackifier, and of one film former chosen from the propylphenylsilsesquioxane resin and the propylsilsesquioxane wax substituted with alkyl units having at least 30 carbons, should be such that the glass transition temperature $T_g$ of the mixture has a value equal to or greater than room temperature.

The at least one film former chosen from a propylphenylsilsesquioxane resin and a propylsilsesquioxane wax substituted with alkyl units having at least 30 carbons is present in the cosmetic composition of the invention in an amount ranging from about 0.5% to about 50% by weight; such as from about 1% to about 30% by weight; such as from about 2% to about 20% by weight, all weights based on the weight of the composition as a whole.

Liquid Fatty Phase

The cosmetic compositions of the present invention comprise a liquid fatty phase. The liquid fatty phase must comprise at least one volatile hydrocarbon oil. Additional compounds which may be present include a volatile silicone oil, a volatile non-silicone oil other than a hydrocarbon oil, and a non-volatile oil such as a non-volatile silicone oil or a non-volatile non-silicone oil.

In one embodiment, the compositions of the present invention are substantially free of volatile silicone oils (i.e., contain less than about 0.1% volatile silicone oils). In another embodiment, the compositions are substantially free of non-volatile oils (i.e., contain less than about 0.1% non-volatile oils).

Suitable volatile silicone oils include, but are not limited to, linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |

TABLE 1-continued

| Compound | Flash Point (° C.) | Viscosity (cSt) |
| --- | --- | --- |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Examples of non-volatile oils that may be used in the present invention include non-volatile silicone oils such as linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes, 2-phenylethyl trimethylsiloxysilicates, trimethyl pentaphenyl trisiloxane, tetramethyl hexaphenyl trisiloxane.

Examples of other non-volatile oils which can be used in the compositions of the present invention include polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

The liquid fatty phase is present in the cosmetic composition of the invention in an amount of from about 10% to about 90% by weight, such as from about 20% to about 80% by weight, such as from about 30% to about 70% by weight, all weights based on the weight of the composition as a whole.

Colorant

The cosmetic compositions of the present invention also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77, 499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the cosmetic compositions of the invention will depend on the color, intensity and use of the cosmetic composition and, as a result, will be determined by those skilled in the art of cosmetic formulation.

Optional Ingredients

In the event the cosmetic composition also contains water, an emulsifier will also be employed in the composition.

Water

Water may be present in the cosmetic composition of the invention in an amount ranging from about 5% to about 75% by weight, such as from about 15% to about 50% by weight, such as from about 20% to about 40% by weight, all weights based on the weight of the composition as a whole.

Emulsifier

Emulsifiers typically employed in the cosmetic compositions of the present invention include anionic, nonionic and cationic emulsifiers. See, e.g., *Encyclopedia of Chemical Technology, KIRK-OTHMER*, volume 22, pp. 333-432, 3rd edition, 1979, Wiley, for the definition of the properties and (emulsifying) functions of the emulsifiers, in particular pp. 347-377 of this publication regarding anionic and nonionic emulsifiers. Examples of nonionic emulsifiers useful in the compositions of the invention include fatty acids, fatty alcohols, polyethoxylated fatty alcohols or polyglycerolated fatty alcohols, such as polyethoxylated stearyl alcohols or cetylstearyl alcohols, esters of fatty acid and sucrose, and glucose alkyl esters, in particular polyoxyethylenated $C_1$-$C_6$ alkyl glucose fatty esters, and ethoxylated compounds such as Polysorbate-20, Laureth-7, Laureth-4 and Sepigel® 305. Examples of anionic emulsifiers include $C_{16}$-$C_{30}$ fatty acids neutralized by amines, ammonia or the alkali metal salts thereof. Examples of cationic emulsifiers include quaternary amines, amine oxides and amines, e.g., alkyl amines, alkyl imidazolines, ethoxylated amines, quaternary compounds, and quaternized esters. Cationic emulsifiers may also provide a conditioning effect.

Organosilicone emulsifiers are particularly useful, particularly in embodiments wherein the emulsion is a water-in-oil (silicone) emulsion. Such emulsifiers include silicone polyethers and polyalkoxylated silicone elastomers.

Silicone polyethers contain alkoxy units. Examples of silicone polyethers include PEG/PPG-18/18 Dimethicone, available as a blend with cyclopentasiloxane as DC5225C or DC5185, PEG-9 Dimethicone, available as KF6017 or KF6028 from Shin-Etsu, cetyl dimethicone copolyol-polyglyceryl-4-isostearate-hexylaurate available as ABIL® WE 09 from Goldschmidt Chemical Corporation, Hopewell, Va., Cetyl Dimethicone Copolyol (ABIL® EM 90), (ABIL® EM 97), Laurylmethicone Copolyol (5200), Cyclomethicone (and) Dimethicone Copolyol available as DC 3225 C from Dow Corning, and Cyclopentasiloxane and Dimethicone Copolyol available as GE SF 1528 from GE Silicones.

Polyalkoxylated silicone elastomers are cross-linked organopolysiloxanes that contain at least one residue such as a polyoxyalkylene residue. Suitable polyoxyalkylenated silicone elastomers that may be used include, but are not limited to, those sold under the names "KSG-21", "KSG-20", "KSG-30", "KSG-31", "KSG-32", "KSG-33", "KSG-210", "KSG-310", "KSG-320", "KSG-330", "KSG-340" and "X-226146" by the company Shin-Etsu, or "DC9010" and "DC9011" by the company Dow Corning.

The emulsifier is generally present in the cosmetic composition of the invention in an amount ranging from about 0.1% to about 10% by weight; such as from about 0.2% to about 7% by weight; such as from about 0.2% to about 5% by weight, all weights based on the weight of the composition as a whole.

Waxes

In some embodiments, it may be desirable to formulate cosmetic compositions in accordance with the present invention with other waxes in addition to the propylsilsesquioxane wax substituted with alkyl units having at least 30 carbons. Suitable waxes are those generally used in cosmetics and dermatology. Examples thereof include, but are not limited to, those of natural origin such as beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil. Examples of suitable synthetic waxes include, but are not limited to, polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly(di)methylsiloxanes and/or poly(di)methyl-siloxane esters that are solid at 40° C., for example, at above 55° C.

The additional waxes may be present in the cosmetic composition of the invention in an amount of from about 0.5% to about 20%, such as from about 1% to about 10% by weight, all weights based on the weight of the composition as a whole.

Gelling Agents

The cosmetic compositions of the invention may also be optionally gelled with an oil-phase gelling agent. The gelling agent increases the liquid fatty phase viscosity and leads to a solid or flowable composition when introduced in said fatty phase. The gelling agent does not encompass waxes, in the sense that it is not waxy. The at least one gelling agent may be chosen from gelling agents in polymeric form and gelling agents in mineral form. The gelling agent may be chosen from agents that gel via chemical cross-linking and agents that gel via physical cross-linking.

Modified clays may be used as gelling agents, examples of which include, but are not limited to, hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox.

Other mineral gelling agents, which can be used in the invention, include silica, such as fumed silica. The fumed silica may have a particle size, which may be nanometric to micrometric, for example ranging from 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300" and "Aerosil 380®" by the company Degussa, and "CAB-O-SIL HS-5", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be: trimethylsiloxyl groups, which are obtained in particular by treating fumed silica in the presence of hexamethyldisilazane. Silicas thus treated are known as "silica silylate" according to the CTFA dictionary (6th edition, 1995). They are sold or made, for example, under the references "Aerosil R812" by the company Degussa and "CAB-O-SIL TS-530" by the company Cabot; dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA dictionary (6th edition, 1995). They are sold or made, for example, under the references "Aerosil R972" and "Aerosil R974" by the company Degussa, and "CAB-O-SIL TS-610®" and "CAB-O-SIL TS-720®" by the company Cabot; groups derived from reacting fumed silica with silane alkoxides or siloxanes. These treated silicas are, for example, the products sold or made under the reference "Aerosil R805®" by the company Degussa.

According to the invention, hydrophobic silica, such as fumed silica, may be used as a lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one lipophilic gelling agent can allow the exudation of the composition to be limited and can allow its stability to be increased, while at the same time conserving the composition's glossy appearance, which is not possible with waxes such as those used conventionally in cosmetics and dermatology.

The at least one gelling agent, if used, will typically be present in the cosmetic composition of the invention in an amount of from about 0.1% to about 20% by weight, such as from about 0.1% to about 15% by weight, such as from about 0.1% to about 10% by weight, all weights based on the weight of the composition as a whole.

The present invention does not require the use of a plasticizer. Consequently, in a preferred embodiment, the composition is substantially free of a plasticizer, i.e., the plasticizer is present in the composition of the invention in an amount of less than about 0.5% by weight, based on the weight of the composition as a whole. Plasticizers are organic compounds added to a high molecular weight polymer both to facilitate processing and to increase the flexibility and toughness of the final product by internal modification of the polymer molecule. Examples of plasticizers include, but are not limited to, oils, cellulose esters, phthalate esters, adipate esters, sebacate esters, tricresyl phosphate, castor oil, glycol ethers, benzyl alcohol, triethyl citrate, and propylene carbonate.

Representative examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Mixtures of preservatives may certainly be used, e.g., the mixture of methyl-paraben, ethylparaben, propylparaben and butylparaben sold under the name Nipastat by Nipa, and the mixture of phenoxyethanol, methylparaben, ethylparaben, propylparaben and butylparaben sold under the name Phenonip, also by Nipa.

The preservatives may be present in the cosmetic composition of the invention in an amount ranging from about 0.01% to about 10% by weight, such as from 0.5% to about 5% by weight, and such as from about 0.8% to about 3% by weight, all weights based on the weight of the composition as a whole.

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.) and mixtures thereof.

The fillers may be present in the cosmetic composition of the invention in an amount ranging from about 0.1% to about 50% by weight, such as from 0.5% to about 30% by weight, and such as from about 1% to about 20% by weight, all weights based on the weight of the composition as a whole.

The compositions of the present invention may further comprise a safe and effective amount of at least one active ingredient or pharmaceutically acceptable salt thereof. The term "safe and effective amount" as used herein, means an amount sufficient to modify the condition to be treated or to deliver the desired skin benefit, while at the same time avoiding serious side effects, at a reasonable benefit to risk ratio within the scope of sound medical judgment. What is a safe and effective amount of the active ingredient will vary with the specific active agent, the ability of the active agent to penetrate through the skin, the age, health and skin condition of the user, and other like factors.

Typically, the active ingredient may be present in the cosmetic composition of the invention in an amount ranging from about 0.01% to about 20% by weight, such as from about 0.1% to about 10% by weight, and such as from about 0.5% to about 5% by weight, all weights based on the weight of the composition as a whole.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically acceptable salts of these active ingredients are useful herein. The following active ingredients are useful in the compositions of the present invention.

The cosmetic compositions of the present invention may also contain sunscreens, which are chemical absorbers that actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol® 1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

Examples of suitable sunscreens include, but are not limited to: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomethyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

The sunscreens will typically be present in the cosmetic composition of the invention in an amount of up to about 30% by weight, based on the weight of the composition as a whole.

The present invention is further described in terms of the following non-limiting examples. Unless otherwise indicated, all parts and percentages are on a weight-by-weight percentage basis.

EXAMPLES

Example 1

Inventive Composition

|    | Trade Name        | INCI Name                                                                                     | w/w % |
|----|-------------------|-----------------------------------------------------------------------------------------------|-------|
| A1 |                   | Isododecane                                                                                   | 10.0  |
| A1 | Silsesquioxane wax | Propylsilsesquioxane wax substituted with alkyl units having at least 30 carbons (Dow Corning) | 4.0   |
| A2 |                   | Isododecane                                                                                   | 20.0  |
| A2 | Regalite R1100    | Hydrogenated Styrene/Methyl Styrene/Indene Copolymer                                          | 12.0  |
| A2 | ABIL EM 90        | Cetyl PEG/PPG-10/1 Dimethicone                                                                | 2.0   |
| B1 |                   | Pigment grind 114                                                                             | 11.5  |
| B2 | KSG 710           | Dimethicone and Dimethicone/Polyglycerin-3 Crosspolymer                                       | 6.0   |

-continued

| | Trade Name | INCI Name | w/w % |
|---|---|---|---|
| B3 | SUNSPHERE H 51 | Silica | 3.0 |
| B3 | ORGASOL 2002 | Nylon-12 | 1.0 |
| C1 | | Glycerin | 3.0 |
| C1 | | Phenoxyethanol | 0.4 |
| C1 | | DI WATER | 27.1 |
| | | TOTAL: | 100.0 |

Pigment Grind 114

| | | w/w % |
|---|---|---|
| Titanium Dioxide | Titanium Dioxide (and) Disodium Stearoyl Glutamate (and) Aluminum Hydroxide | 6.80 |
| Iron Oxide - Yellow | Iron Oxides (and) Disodium Stearoyl Glutamate (and) Aluminum Hydroxide | 2.24 |
| Iron Oxide - Red | Iron Oxides (and) Disodium Stearoyl Glutamate (and) Aluminum Hydroxide | 0.51 |
| Iron Oxide - Black | Iron Oxides (and) Disodium Stearoyl Glutamate (and) Aluminum Hydroxide | 0.45 |
| Cyclomethicone | Cyclomethicone | 3.50 |

Example 2

Comparative Composition

| Phase | Trade Name | INCI Name | w/w % |
|---|---|---|---|
| A1 | DC-245 | Cyclopentasiloxane | 31.0 |
| A1 | Silsesquioxane wax | Propylsilsesquioxane wax substituted with alkyl units having at least 30 carbons (Dow Corning) | 4.0 |
| A2 | ABIL EM 90 | Cetyl PEG/PPG-10/1 Dimethicone | 2.0 |
| B1 | | Pigment grind 93 | 15.0 |
| B2 | KSG 710 | Dimethicone and Dimethicone/Polyglycerin-3 Crosspolymer | 6.0 |
| B3 | SUNSPHERE H 51 | Silica | 3.0 |
| B3 | ORGASOL 2002 | Nylon-12 | 1.0 |
| C1 | | Glycerin | 5.0 |
| C1 | | Phenoxyethanol | 0.4 |
| C1 | | DI WATER | 32.6 |
| | | TOTAL | 100.0 |

Pigment Grind 93

| | | w/w % |
|---|---|---|
| Titanium Dioxide | Titanium Dioxide (and) Disodium Stearoyl Glutamate (and) Aluminum Hydroxide | 6.80 |
| Iron Oxide - Yellow | Iron Oxides (and) Disodium Stearoyl Glutamate (and) Aluminum Hydroxide | 2.24 |
| Iron Oxide - Red | Iron Oxides (and) Disodium Stearoyl Glutamate (and) Aluminum Hydroxide | 0.51 |
| Iron Oxide - Black | Iron Oxides (and) Disodium Stearoyl Glutamate (and) Aluminum Hydroxide | 0.45 |
| Cyclomethicone | Cyclomethicone | 5.00 |

The inventive composition containing the tackifier Regalite® R1100 and the propylsilsesquioxane wax substituted with alkyl units having at least 30 carbons exhibited improved transfer resistance and wear as compared to the comparative composition having no tackifier. Furthermore, the inventive composition was surprisingly less tacky than the comparative composition.

Example 3

Lip Composition

| Phase | Trade Name | INCI Name | w/w % |
|---|---|---|---|
| A | PERMETHYL 99A | Isododecane | 38.82 |
| | Regalite R1100 | Hydrogenated Styrene/Methyl Styrene/Indene Copolymer | 40.00 |
| | DC XX-8005 | Propylsilsesquioxane wax substituted with alkyl units having at least 30 carbons | 3.00 |
| B | PERMETHYL 99A | Isododecane | 7.64 |
| | Pigment blend | Iron Oxides | 0.38 |
| | | Titanium dioxide | 1.37 |
| | | red/brown iron oxide | 2.35 |
| | | Red #7 | 1.74 |
| | Bentone gel ISD V | Disteardimonium Hectorite | 0.70 |
| C | Silica (and) Dimethicone (93/7) | Silica | 2.00 |
| | | Mica | 2.00 |
| | | TOTAL | 100.00 |

Example 4

Lip Composition

| Phase | Trade Name | INCI Name | w/w % |
|---|---|---|---|
| A | PERMETHYL 99A | Isododecane | 32.15 |
| | Regalite R1100 | Hydrogenated Styrene/Methyl Styrene/Indene Copolymer | 40.00 |
| | DC XX5012 | Isododecane (and) Propylsilsesquioxane Resin | 6.67 |
| | DC XX-8005 | Propylsilsesquioxane wax substituted with alkyl units having at least 30 carbons | 3.00 |
| B | PERMETHYL 99A | Isododecane | 7.64 |
| | Pigment blend | Iron Oxides | 0.38 |
| | | Titanium dioxide | 1.37 |
| | | red/brown iron oxide | 2.35 |
| | | Red #7 | 1.74 |
| | Bentone gel ISD V | Disteardimonium Hectorite | 0.70 |
| C | Silica (and) Dimethicone (93/7) | Silica | 2.00 |
| | | Mica | 2.00 |
| | | TOTAL | 100.00 |

Example 5

Lip Composition

| Phase | Trade Name | INCI Name | w/w % |
|---|---|---|---|
| A | PERMETHYL 99A | Isododecane | 35.49 |
| | Regalite R1100 | Hydrogenated Styrene/Methyl Styrene/Indene Copolymer | 30.00 |

-continued

| Phase | Trade Name | INCI Name | w/w % |
|---|---|---|---|
| | DC XX5012 | Isododecane (and) Propylsilsesquioxane Resin | 13.33 |
| | DC XX-8005 | Propylsilsesquioxane wax substituted with alkyl units having at least 30 carbons | 3.00 |
| B | PERMETHYL 99A | Isododecane | 7.64 |
| | Pigment blend | Iron Oxides | 0.38 |
| | | Titanium dioxide | 1.37 |
| | | red/brown iron oxide | 2.35 |
| | | Red #7 | 1.74 |
| | Bentone gel ISD V | Disteardimonium Hectorite | 0.70 |
| C | Silica (and) Dimethicone (93/7) | Silica | 2.00 |
| | | Mica | 2.00 |
| | | TOTAL | 100.00 |

Example 6

Lip Composition

| Phase | Trade Name | INCI Name | w/w % |
|---|---|---|---|
| A | PERMETHYL 99A | Isododecane | 30.82 |
| | Regalite R1100 | Hydrogenated Styrene/Methyl Styrene/Indene Copolymer | 20.00 |
| | DC XX5012 | Isododecane (and) Propylsilsesquioxane Resin | 27.00 |
| | DC XX-8005 | Propylsilsesquioxane wax substituted with alkyl units having at least 30 carbons | 4.00 |
| B | PERMETHYL 99A | Isododecane | 7.64 |
| | Pigment blend | Iron Oxides | 0.38 |
| | | Titanium dioxide | 1.37 |
| | | red/brown iron oxide | 2.35 |
| | | Red #7 | 1.74 |
| | Bentone gel ISD V | Disteardimonium Hectorite | 0.70 |
| C | Silica (and) Dimethicone (93/7) | Silica | 2.00 |
| | | Mica | 2.00 |
| | | TOTAL | 100.00 |

Procedure for Examples 3-6:

1. Heat the oil in phase A at 100° C. for 2-5 minutes, before adding Regalite 1100.

2. After oil phase A becomes homogeneous, add the silicone resin and wax and mix at 100° C. until the solution is homogenous.

3. Add color grind of phase B gradually into A and mix for 5 minutes.

4. Add phase C into phase (A+B) and mix for 5 minutes, reduce heat to 50° C., then pour into component.

It is to be understood that the foregoing describes preferred embodiments of the invention and that modifications may be made therein without departing from the spirit or scope of the invention as set forth in the claims.

What is claimed is:

1. A composition comprising:
   (a) at least one tackifier component which is a hydrogenated styrene/methyl styrene/indene copolymer;
   (b) at least one film former comprising:
      (i) a propylsilsesquioxane resin selected from the group consisting of cyclopentasiloxane (and) polypropylsilsesquioxane, and isododecane (and) polypropylsilsesquioxane, and
      (ii) a propylsilsesquioxane wax substituted with alkyl units having at least 30 carbons;
   (c) a liquid fatty phase comprising at least one volatile hydrocarbon;
   (d) at least one colorant;
   (e) optionally, water; and
   (f) optionally, at least one emulsifier.

2. The composition of claim 1, wherein (a) is present in the composition in an amount of from greater than about 0 to about 50% by weight, based on the weight of the composition as a whole.

3. The composition of claim 1, wherein (a) is present in the composition in an amount of from greater than about 0 to about 20% by weight, based on the weight of the composition as a whole.

4. The composition of claim 1, wherein (b) is present in the composition in an amount of from about 0.5 to about 50% by weight, based on the weight of the composition as a whole.

5. The composition of claim 1, wherein (b) is present in the composition in an amount of from about 2 to about 20% by weight, based on the weight of the composition as a whole.

6. The composition of claim 1, wherein (c) is present in the composition in an amount of from about 10 to about 90% by weight, based on the weight of the composition as a whole.

7. The composition of claim 1, wherein (c) is present in the composition in an amount of from about 30 to about 70% by weight, based on the weight of the composition as a whole.

8. The composition of claim 1, wherein (e) is present in the composition in an amount of from about 5 to about 75% by weight, based on the weight of the composition as a whole.

9. The composition of claim 1, wherein (e) is present in the composition in an amount of from about 20 to about 40% by weight, based on the weight of the composition as a whole.

10. The composition of claim 1, wherein the composition is substantially free of a plasticizer.

11. A method of making up keratinous substrates comprising applying onto the keratinous substrates a composition containing:
    (a) at least one tackifier component which is a hydrogenated styrene/methyl styrene/indene copolymer;
    (b) at least one film former comprising:
       (i) a propylsilsesquioxane resin selected from the group consisting of cyclopentasiloxane (and) polypropylsilsesquioxane, and isododecane (and) polypropylsilsesquioxane, and
       (ii) a propylsilsesquioxane wax substituted with alkyl units having at least 30 carbons;
    (c) a liquid fatty phase comprising at least one volatile hydrocarbon;
    (d) at least one colorant;
    (e) optionally, water; and
    (f) optionally, at least one emulsifier.

12. The method of claim 11, wherein (a) is present in the composition in an amount of from greater than about 0 to about 50% by weight, based on the weight of the composition as a whole.

13. The method of claim 11, wherein (a) is present in the composition in an amount of from greater than about 0 to about 20% by weight, based on the weight of the composition as a whole.

14. The method of claim 11, wherein (b) is present in the composition in an amount of from about 0.5 to about 50% by weight, based on the weight of the composition as a whole.

15. The method of claim 11, wherein (b) is present in the composition in an amount of from about 2 to about 20% by weight, based on the weight of the composition as a whole.

16. The method of claim 11, wherein (c) is present in the composition in an amount of from about 10 to about 90% by weight, based on the weight of the composition as a whole.

17. The method of claim 11, wherein (c) is present in the composition in an amount of from about 30 to about 70% by weight, based on the weight of the composition as a whole.

18. The method of claim 11, wherein (e) is present in the composition in an amount of from about 5 to about 75% by weight, based on the weight of the composition as a whole.

19. The method of claim 11, wherein (e) is present in the composition in an amount of from about 20 to about 40% by weight, based on the weight of the composition as a whole.

20. The method of claim 11, wherein the composition is substantially free of a plasticizer.

* * * * *